US007767214B2

United States Patent
Simon et al.

(10) Patent No.: US 7,767,214 B2
(45) Date of Patent: *Aug. 3, 2010

(54) GONIOCHROMATIC/LIGHT REFLECTIVE COSMETIC MAKEUP COMPOSITIONS

(75) Inventors: Jean-Christophe Simon, Paris (FR); Franck Girier-Dufournier, Paris (FR); Patricia Lemann, Creteil (FR)

(73) Assignee: L'Oreal, Paris (FR)

( * ) Notice: Subject to any disclaimer, the term of this patent is extended or adjusted under 35 U.S.C. 154(b) by 583 days.

This patent is subject to a terminal disclaimer.

(21) Appl. No.: 10/622,480

(22) Filed: Jul. 21, 2003

(65) Prior Publication Data

US 2005/0118122 A1    Jun. 2, 2005

Related U.S. Application Data

(60) Provisional application No. 60/399,443, filed on Jul. 31, 2002.

(30) Foreign Application Priority Data

Jul. 19, 2002    (FR) .................................. 02 09245

(51) Int. Cl.
  *A61K 8/02*    (2006.01)
  *A61K 8/00*    (2006.01)
(52) U.S. Cl. ............................ 424/401; 424/63; 424/64
(58) Field of Classification Search ................ 424/401, 424/63, 64
  See application file for complete search history.

(56) References Cited

U.S. PATENT DOCUMENTS

| 6,267,810 | B1 |   | 7/2001  | Pfaff et al. |
|---|---|---|---|---|
| 6,325,847 | B1 |   | 12/2001 | Christie et al. |
| 6,428,773 | B1 |   | 8/2002  | Oko et al. |
| 6,451,294 | B1 | * | 9/2002  | Simon ........................... 424/63 |
| 6,491,932 | B1 | * | 12/2002 | Ramin et al. ................ 424/401 |
| 6,663,852 | B2 |   | 12/2003 | Simon et al. |
| 6,759,052 | B1 | * | 7/2004  | Suzuki et al. ................ 424/401 |
| 2002/0064509 | A1 |   | 5/2002 | Grimm et al. |
| 2003/0019501 | A1 |   | 1/2003 | Hirota et al. |
| 2004/0076649 | A1 | * | 4/2004 | Blin et al. .................... 424/401 |
| 2004/0076650 | A1 |   | 4/2004 | Blin et al. |
| 2004/0105827 | A1 |   | 6/2004 | Grimm et al. |
| 2004/0241118 | A1 |   | 12/2004 | Simon et al. |

FOREIGN PATENT DOCUMENTS

| EP | 0 953 330 A2 |   | 11/1999 |
|---|---|---|---|
| EP | 1082952 A1 | * | 3/2001 |
| EP | 1 195 155 A2 |   | 4/2002 |
| FR | 2777178 A1 | * | 10/1999 |
| FR | 2816830 A1 | * | 5/2002 |
| JP | 11-322541 |   | 11/1999 |
| JP | 2000-198944 |   | 7/2000 |
| JP | 2001-270805 A |   | 10/2001 |
| JP | 2002-080326 |   | 3/2002 |
| JP | 2002-155241 |   | 5/2002 |
| JP | 2002-249415 |   | 9/2002 |
| JP | 2004-161744 A |   | 6/2004 |
| KR | 10-2004-0010254 |   | 10/2004 |
| WO | WO 98/53011 A1 |   | 11/1998 |
| WO | 99/66883 A3 |   | 12/1999 |
| WO | WO 00/49995 A2 |   | 8/2000 |
| WO | WO 00/75240 A1 |   | 12/2000 |
| WO | WO 01/51015 A2 |   | 7/2001 |
| WO | WO 02/28356 A1 |   | 4/2002 |
| WO | WO 02/41855 A1 |   | 5/2002 |

OTHER PUBLICATIONS

Journal of Technical Disclosure, Jun. 18, 2002, pp. 1-6, 2002-500620, Japan.
French Search Report Issued in French Counterpart Application FR 02/09245 Issued Apr. 2, 2003, 3 Pages.
Product brochure, Presperse, Inc., 4 pages, received Apr. 1999 in U.S. Appl. No. 09/482,586, now Oko et al. U.S. 6,428,773 B1 (obtained from file history).

* cited by examiner

*Primary Examiner*—Gina C. Yu
(74) *Attorney, Agent, or Firm*—Buchanan Ingersoll & Rooney PC

(57) ABSTRACT

Goniochromatic/light reflecting cosmetic compositions well suited for making up the skin, lips, hair or integuments, contain (a) at least one goniochromatic coloring agent and (b) an amount of light reflective particles different from said at least one goniochromatic coloring agent and selected from the group consisting of (i) particles of a natural or synthetic substrate at least partially coated with at least one layer of at least one metal, (ii) particles of a synthetic substrate at least partially coated with at least one layer of at least one metallic compound, (iii) particles which comprise a stack of at least two layers of materials having different refractive indices, at least one of such layers optionally comprising a polymer, and (iv) metal oxide particles, formulated into (c) a topically applicable, physiologically acceptable medium therefor.

61 Claims, 2 Drawing Sheets

GONIOCHROMATIC/LIGHT REFLECTIVE COSMETIC MAKEUP COMPOSITIONS

CROSS-REFERENCE TO PRIORITY/PROVISIONAL APPLICATIONS

This application claims priority under 35 U.S.C. § 119 of FR-02/09245, filed Jul. 19, 2002, and of provisional application Ser. No. 60/399,443, filed Jul. 31, 2002, both hereby expressly incorporated by reference. This application is also a continuation of said '443 provisional.

CROSS-REFERENCE TO RELATED APPLICATION

Our copending application Ser. No. 10/622,478, filed concurrently herewith and assigned to the assignee hereof.

BACKGROUND OF THE INVENTION

1. Technical Field of the Invention

The present invention relates to making up the skin, for example that of the face or the body, the lips or integuments such as the eyelashes, the eyebrows, the nails and the hair.

2. Description of Background/Related/Prior Art

Makeup compositions, for instance free powders, foundations, nail varnishes, mascaras, makeup rouges, eye shadows, lipsticks, glosses in a jar or liquid glosses, generally consist of a physiologically acceptable medium and various coloring agents.

Consumers have long been seeking compositions for remodeling the face, in particular for highlighting the cheekbones and/or for making the lips full. There is not at the present time an effective solution for satisfying this expectation.

It is known that a volumizing effect may be produced by applying a light shade and a dark shade next to each other, the light shade being applied to the area that it is desired to highlight. Producing this effect traditionally requires the use of two different compositions and depends on the skill of the person applying them. This technique is more difficult to carry out for making up the lips.

Recently, the capacity naturally manifested by goniochromatic pigments to change color depending on the angle of observation and/or of incidence of the light has been exploited in the cosmetics field. Thus, EP-A-0 953,330, assigned to the assignee hereof, describes a makeup kit combining a first goniochromatic pigment and a second pigment containing one of the colors of the first pigment. This combination affords novel colored effects without, however, substantially modifying the perception of the volume of the part of the body onto which it is applied.

Moreover, WO 01/51015 proposes compositions combining conventional interference pigments with a four-layer interference pigment, also known as a "shadow pigment", which has a variable coloration depending on the angle of specular reflection. This is reflected on the treated support by a color change between light and dark. These compositions improve the perception of the contour of the various parts of the face or body, but they do not create a satisfactory volumizing effect.

There is consequently a need for a cosmetic composition capable of affording a satisfactory impression of volume.

SUMMARY OF THE INVENTION

The present invention features compositions for obtaining novel makeup effects, and especially makeup compositions that create an optical volumizing effect once applied to a support or substrate such as the skin, the lips or the integuments. After application, for example to the cheeks, the eyelids or the lips, these compositions afford a perception of volume that is different from that of the support without makeup. Such an effect may be termed "three-dimensional" and more particularly a "pulping" effect for the lips or a "morphing" effect for the face and the body.

According to one of its aspects, the present invention thus features cosmetic compositions comprising, in a physiologically acceptable medium, at least one goniochromatic coloring agent and at least some reflective particles that are different from the goniochromatic coloring agent, selected from the group consisting of:

particles with a natural or synthetic substrate coated at least partially with at least one layer of at least one metal, particles with a synthetic substrate coated at least partially with at least one layer of at least one metallic compound and especially a metal oxide, particles formed from a stack of at least two layers of materials with different refractive indices, at least one of these layers possibly being a polymer, and metal oxide particles.

BRIEF DESCRIPTION OF THE DRAWING

FIG. 1 also shows for comparative purposes the color path for a Summit Gold YD30D nacre sold by Engelhard.

DETAILED DESCRIPTION OF BEST MODE AND SPECIFIC/PREFERRED EMBODIMENTS OF THE INVENTION

It has been found that the combination of a goniochromatic coloring agent and reflective particles as defined above makes it possible, unexpectedly, to create or reinforce the impression of volume, the reflective particles generating highlight points that are visible to the naked eye when the composition is applied to form a layer on a support and illuminated.

The term "cosmetic composition" denotes a composition as defined in Directive 93/35/EEC of the Counsel of 14 Jun. 1993.

The term "physiologically acceptable medium" denotes a non-toxic medium that may be applied to human skin, lips or integuments.

For the purposes of the present invention, the term "goniochromatic coloring agent" denotes an agent for obtaining, when the cosmetic composition is spread onto a support, a color trajectory in the a*b* plane of the CIE 1976 colorimetric space corresponding to a variation Dh of the hue angle h of at least 20° when the angle of observation relative to the normal is varied between 0° and 80°, for an incident light angle of 45°.

The color trajectory may be measured, for example, using an Instrument Systems brand spectrogonioreflectometer of reference GON 360 Goniometer, after the cosmetic composition has been spread in fluid form to a thickness of 300 µm using an automatic spreader onto an Erichsen brand contrast card of reference Typ 24/5, the measurement being performed on the black background of the card.

Figure 1:
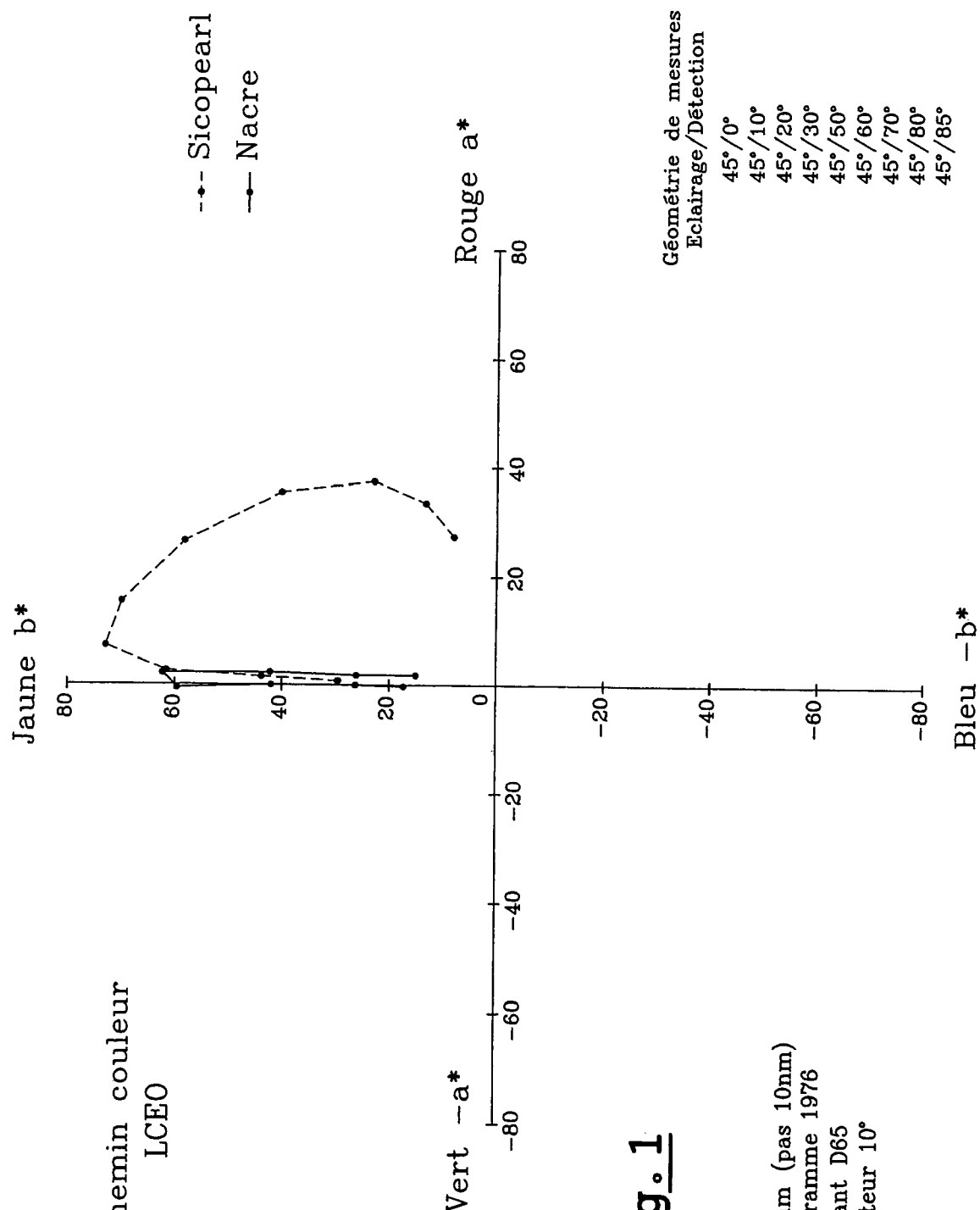
FIG. 1 shows a color trajectory obtained with spectrogonioreflectometer for a liquid gloss prepared in accordance with the invention, comprising Sicopearl® goniochromatic pigments sold by BASF.

By way of example, FIG. 1 shows a color trajectory obtained with such a spectrogonioreflectometer for a liquid gloss prepared in accordance with the invention, comprising Sicopearl® goniochromatic pigments sold by BASF.

For the purpose of the present invention, a goniochromatic coloring agent makes it possible to observe a color change, also known as a "color flop", as a function of the angle of observation, which is greater than the change that may be encountered with nacres.

FIG. 1 also shows for comparative purposes the color path for a Summit Gold YD30D nacre sold by Engelhard.

For the purpose of the present invention, the term "reflective particles" denotes particles for which the size, structure, in particular the thickness of the layer(s) of which they are composed and their physical and chemical nature, and the surface state, allow them to reflect the incident light with an intensity sufficient to be able to create at the surface of the claimed composition, when said composition is applied to the support to be made up, highlight points that are visible to the naked eye, i.e., more luminous points that contrast with their surroundings by appearing to shine.

Reflective particles can cloud the visual perception of the curvature of the makeup support, by tending to prevent long-lasting visual focusing, the highlight points being capable of appearing or disappearing randomly when the made-up support and the observer are in motion.

As will be specified later, it may prove desirable for the mean gloss of the composition to exceed a certain threshold, especially when the composition is intended to be applied to the lips. The reason for this is that when the composition has a relatively high gloss, the treated support appears to be visually even more detached from its surroundings.

The term "mean gloss" denotes the gloss as may be conventionally measured using a glossmeter, by the following method.

A layer 50 mm in thickness of the composition whose mean gloss it is desired to evaluate is spread, using an automatic spreader, onto a Leneta brand contrast card of reference Form 1A Penopac. The layer covers at least the white background of the card. Measurement of the gloss at 20° is then performed on the white background using a Byk Gardner brand glossmeter of reference microTRI-GLOSS.

The mean gloss of the composition is advantageously greater than or equal to 30, or even 50 and better still 70, especially when the composition is intended to be applied to the lips.

The composition may comprise a gloss base intended to allow the desired mean gloss to be obtained.

For the purpose of the present invention, the term "base" denotes the cosmetic composition without the goniochromatic coloring agent(s) and without the reflective particles.

The cosmetic composition may thus comprise, in one embodiment, a base whose mean gloss is greater than 20, or even 50 and better still 70, especially in the case of a composition intended to be applied to the lips. The presence of the goniochromatic coloring agent(s) and of the reflective particles in the gloss base may result in a cosmetic composition whose mean gloss may or may not be different from the mean gloss of the base considered in isolation.

The formulation of the base will depend on the use for which the cosmetic composition is intended and on the form in which the cosmetic composition is provided.

The formulation of the base may thus be different depending on whether the cosmetic composition is intended to form a liquid gloss or a lipstick, for example. A lipstick base with a mean gloss of about 60, a liquid gloss base or an eyeshadow base with a mean gloss of about 70, and a nail varnish base with a mean gloss of about 50 may be chosen, for example.

The term "liquid gloss", also known as liquid lipstick or lipgloss, denotes a fluid product intended to be applied to the lips and packaged, for example, in a container provided with an applicator, this applicator comprising a handle member that also serves as a cap for closing the container, and an applicator component.

The cosmetic composition may comprise, especially in the case where it is intended to be applied to the lips, an oily phase, especially an oily phase with a refractive index of between 1.47 and 1.51, which can allow a relatively high gloss to be obtained.

The use of a gloss base constitutes only one means among others for obtaining a cosmetic composition with gloss. It would not constitute a departure from the context of the present invention if, before or after a cosmetic composition in accordance with the invention has been applied, for example to the lips, a transparent gloss composition that does not prevent the goniochromatic effect and the highlight points from being observed is applied.

The composition may also comprise goniochromatic fibers, so as to produce an additional visual effect.

Besides the goniochromatic coloring agent(s) and the reflective particles, the composition may comprise various other compounds, and especially at least one non-goniochromatic coloring agent.

This non-goniochromatic coloring agent may be chosen, for example, from colorants, monochromatic pigments and nacres, and may be intended, for example, to correct the hues produced by the goniochromatic coloring agent(s) so as to avoid the appearance of colors deemed undesirable. The non-goniochromatic coloring agent may also be present in the cosmetic composition to give it a desired color under certain observation conditions.

According to another of its aspects, this invention features the use of at least one goniochromatic coloring agent in combination with reflective particles, to makeup the skin, the lips or the integuments.

The present invention also features the use, for making up the skin, the lips or the integuments, of at least one goniochromatic coloring agent in combination with reflective particles that are different from the goniochromatic coloring agent and selected from the group consisting of: particles with a natural or synthetic substrate, coated at least partially with at least one layer of at least one metal, particles with a synthetic substrate coated at least partially with at least one layer of at least one metallic compound and especially a metal oxide, particles formed from a stack of at least two layers of different refractive indices, especially two layers of polymers, and metal oxide particles.

According to another of its aspects, the invention also features the use of at least one goniochromatic coloring agent capable of creating a goniochromatic colored background and of reflective particles capable of creating on the support highlight points that are visible to the naked eye, in a makeup composition intended to create or reinforce the volume of a support such as the skin, the lips or the integuments, for example the nails or keratin fibers, onto which support the said goniochromatic coloring agent and the said reflective particles are applied simultaneously or consecutively.

According to another of its aspects, the invention also relates to a process for making up a support or substrate such as the skin, the lips or the integuments, for example the nails or keratin fibers, comprising the simultaneous or consecutive application onto the support of at least one goniochromatic coloring agent capable of creating a goniochromatic colored background and of reflective particles capable of creating on the support highlight points that are visible to the naked eye, and that are distributed discretely on the goniochromatic colored background.

In one embodiment, the goniochromatic coloring agent and the reflective particles are applied simultaneously in the form of a composition as defined above.

In another embodiment, the regime or regimen process comprises the application onto the support of a first cosmetic composition comprising, in a physiologically acceptable medium, at least one goniochromatic coloring agent, and then of a second cosmetic composition, which is different from the first composition and which comprises at least some reflective particles. Although the order of application of the first and second compositions indicated above is preferential, it would not constitute a departure from the context of the present invention to invert this order, provided that the reflective particles can create highlight points that are visible to the naked eye, after applying the two compositions to the support.

At least either the first or the second composition can comprise a gloss base as defined above. A third transparent glossy composition may also be applied over the first and second compositions.

According to another of its aspects, this invention features a regime or regimen for making up a support chosen from the skin, the lips and the integuments, comprising the simultaneous or consecutive application to the support of at least one goniochromatic coloring agent and of reflective particles that are different from the goniochromatic coloring agent and selected from the group consisting of: particles with a natural or synthetic substrate, coated at least partially with at least one layer of at least one metal, particles with a synthetic substrate coated at least partially with at least one layer of at least one metallic compound and especially a metal oxide, particles formed from a stack of at least two layers with different refractive indices, especially two layers of polymers, and metal oxide particles.

According to another of its aspects, the present invention also relates to a makeup kit for a support chosen from the skin, the lips and the integuments, comprising a first and a second cosmetic composition that are different from each other. The first composition comprises at least some reflective particles selected from the group consisting of: particles comprising a natural or synthetic substrate, coated at least partially with a layer of at least one metal, particles with a synthetic substrate coated at least partially with at least one layer of a metallic compound and especially a metal oxide, particles formed from a stack of at least two layers with different refractive indices, especially two layers of polymers, and metal oxide particles. The second composition comprises, in a physiologically acceptable medium, at least one goniochromatic coloring agent. The first and second compositions are packaged separately.

Another embodiment of the invention is a makeup kit for a support chosen from the skin, the lips and the integuments, comprising a first and a second composition that are different from each other, the first composition comprising at least some reflective particles and a second composition comprising, in a physiologically acceptable medium, at least one goniochromatic coloring agent, the first and second compositions being packaged separately, the reflective particles being capable of creating highlight points that are visible to the naked eye, after applying the two compositions to the support.

The characteristics described above, especially regarding the mean gloss, are also valid for either the first or the second composition and for the layer resulting from the application of the first and second compositions.

Examples of Reflective Particles:

The reflective particles used must be compatible with cosmetic use and must be able to remain in the physiologically acceptable medium, and in particular must not dissolve therein, or in any case must not completely dissolve therein.

The reflective particles may be present in the composition in homogeneously dispersed form, for example in a content ranging from 0.1% to 20% relative to the total weight of the composition, preferably from 1% to 15% by weight and better still from 1% to 10% by weight, for example about 2%, especially for a composition intended to be applied to the lips. The content of reflective particles may depend, inter alia, on the nature of the support intended to receive the cosmetic composition, and also on the nature of the physiologically acceptable medium and of the goniochromatic coloring agent (s) and on the nature and size of the reflective particles. The content of reflective particles will preferably be chosen such that the highlight points are discretely distributed over the colored goniochromatic surface. The reflective particles may be in an amount that is sufficient to be able to observe simultaneously, when the cosmetic composition is applied to a support such as the lips, for example, a plurality of highlight points, for example more than about ten, or even more than about fifty, or even more, for example more than one hundred or several hundred.

According to one particular embodiment, the reflective particles may be introduced such that the reflective particles/goniochromatic pigments weight ratio ranges from 0.3 to 3 and in particular from 0.5 to 2.5. In point of fact, this ratio can vary as a function of the nature of the cosmetic composition in which the said particles are incorporated. For example, in a formulation of nail varnish type, this reflective particles/goniochromatic pigments weight ratio may be greater than 1, in particular greater than 1.5 and especially greater than or equal to 2. On the other hand, in formulations of liquid lipstick type or in the form of tubes, this weight ratio may be less than or equal to 2 and especially less than or equal to 1.5.

The reflective particles may be goniochromatic or non-goniochromatic particles, and interference or non-interference particles, but are preferably non-goniochromatic particles.

Their size is compatible with the manifestation of a specular reflection of visible light (400-700 nm) of sufficient intensity, taking into account the mean gloss of the composition, to create a highlight point. This size can vary depending on the chemical nature of the particles, their shape and their power of specular reflection of visible light.

Among the reflective particles that may be used in the invention, some may have a relative difference $\Delta$, defined by the formula $\Delta [L^*_{SCI}-L^*_{SCE}]/L^*_{SCE}$, of greater than or equal to 0.25. For comparative purposes, some nacres that are unsuitable as reflective particles have a coefficient $\Delta$ of less than 0.25. In the above formula, $L^*_{SCI}$ denotes the lightness L* measured using a Minolta brand spectrocolorimeter of reference CM-2002, in "specular component included" mode, and $L^*_{SCE}$ denotes the lightness L* measured using the same machine, in "specular component excluded" mode. To perform the measurements, a dispersion containing 5% by weight of the test particles in a transparent nail varnish of standard composition (essentially nitrocellulose, a resin and a plasticizer) is prepared and a coat 300 μm thick of the composition thus formed is spread in fluid form onto the black background of a contrast card.

The SCI/SCE function of the spectrocolorimeter is used with the geometry d/8 to measure $L^*_{SCI}$ and $L^*_{SCE}$.

By way of example, for reflective particles of Reflecks® brand, sold by Engelhard, comprising a glass substrate coated with brown iron oxide, a relative difference Δ of greater than 0.7 was measured, whereas for Flamenco® nacres sold by the same company, a relative difference of less than 0.2 was measured.

The reflective particles will preferably have a size of at least 10 μm, for example between about 20 μm and about 50 μm.

The term "size" denotes the size given by the statistical particle size distribution to half the population, known as the D50. The size of the reflective particles may depend on their surface state. The more reflective their surface state, the smaller may be the size, in principle, and vice versa.

Out of concern for aesthetics, it is preferable, except when they shine to create highlight points, for the reflective particles not to be perceptible at all or not readily perceptible to the naked eye at the surface of the composition applied to its support. It is also desirable for the reflective particles not to have sizes such that they give rise to a sensation of discomfort on the support. The use of particles less than or equal to 250 μm and better still less than or equal to 150 μm and for example less than 100 μm in size is thus preferred. The size of the particles may also depend on the nature of the support to which the composition is intended to be applied; certain parts of the body or the face may, for example, tolerate larger sizes better than others without giving rise to discomfort.

The reflective particles may be in varied forms. These particles may especially be in the form of platelets or globular, in particular spherical.

The term "platelet form" denotes particles for which the ratio of the longest size to the thickness is greater than or equal to 5, or even 10, or better still 20. The thickness of the particles in platelet form is, for example, between about 0.5 μm and about 5 μm.

Particles with a substantially flat outer surface are most particularly suitable, since they can give rise more readily, if their size, structure and surface state allow it, to an intense specular reflection. This is referred to as a mirror effect.

For such particles in particular, it is essentially the light returned by reflection in a direction forming, with the normal to the reflective surface, the same angle as that formed by the incident light with this normal, which allows these particles to appear as highlight points, rather than the light scattered in the other directions.

It may be desirable for the reflective particles to be non-scattering and non-matt.

It may also be desirable for the reflective particles not to substantially adversely effect the coloration of the cosmetic composition.

In this regard, reflective particles that allow a metallic reflection of the incident light are most particularly suitable. This is the case especially when the reflective particles allow, irrespective of their shape, a reflection on a layer of a metal, for example of silver. Such particles are found to be relatively neutral with respect to the color of the composition.

Reflective particles that may be used in the invention, with a metallic or white glint, may, for example, reflect the light in all the components of the visible range without significantly absorbing one or more wavelengths. The spectral reflectance of these reflective particles may, for example, be greater than 70%, and better still at least 80%, or even 90% or 95%, in the 400-700 nm range.

The light reflected by the reflective particles may be non-iridescent, especially in the case of a metallic glint.

Whatever their shape, the reflective particles may or may not have a multilayer structure, and, in the case of a multilayer structure, for example at least one layer of uniform thickness, especially of a reflective material.

When the reflective particles do not have a multilayer structure, they may be composed, for example, of metal oxides, for example titanium oxide or iron oxide, obtained synthetically so as to have a substantially flat surface having, for example, a non-matt and non-scattering surface state, allowing a specular reflection of light that is sufficient to obtain highlight points within the cosmetic composition.

When the reflective particles do have a multilayer structure, these particles may comprise, for example, a natural or synthetic substrate, especially a synthetic substrate at least partially coated with at least one layer of a reflective material.

Whatever the shape of the reflective particles, the substrate may, when it is synthetic, be prepared with a shape that promotes the formation of a reflective surface after coating, especially after depositing a layer of reflective material. The substrate may, for example, have a flat surface and the layer of reflective material a substantially uniform thickness.

The substrate may be made of one or more materials, and solid or hollow. The substrate may be organic or mineral. The substrate may be natural, but a synthetic substrate is preferably used, for the reason indicated above.

The substrate may be chosen from glasses, ceramics, graphite, metal oxides, aluminas, silicas, silicates, especially aluminosilicates and borosilicates and synthetic mica, this list not being limiting.

The reflective material may comprise a layer of metal or of a metallic compound.

The layer of metal or of metallic compound may or may not totally coat the substrate, and the layer of metal may be at least partially coated with a layer of another material, for example a transparent material. It may be preferable for the layer of metal or of metallic compound to totally coat the substrate, directly or indirectly, i.e., with insertion of at least one intermediate metallic or non-metallic layer.

The metal may be chosen, for example, from Ag, Au, Cu, Al, Ni, Sn, Mg, Cr, Mo, Ti, Pt, Va, Rb, W, Zn, Ge, Te, Se and alloys thereof. Ag, Au, Al, Zn, Ni, Mo, Cr, Cu and alloys thereof (for example bronzes and brasses) are preferred metals.

In the case especially of particles with a substrate coated with silver or gold, the metallic layer may be present in a content representing, for example, from 0.1% to 50% or even between 1% and 20% of the total weight of the particles.

Particles of glass coated with a metallic layer may have a size ranging, for example, from 10 μm to 300 μm and better still from 25 μm to 150 μm. In the case where these particles are in the form of platelets, the thickness may be, for example, between about 0.1 μm and about 25 μm, preferably from about 0.5 μm to about 10 μm and better still from about 0.5 μm to about 5 μm. In the case where these particles are in the form of spheres, they may have a size ranging, for example, from about 10 to 100 μm.

Particles of glass coated with a metallic layer are described especially in JP-A-09-188,830, JP-A-10-158,450, JP-A-10-158,541, JP-A-07-258,460 and JP-A-05-017,710.

Again as an example of reflective particles comprising a mineral substrate coated with a layer of metal, mention may also be made of particles comprising a borosilicate substrate coated with silver, also known as "white nacres".

Particles with a glass substrate coated with silver, in the form of platelets, are sold under the name Microglass Metashine REFSX 2025 PS by Toyal. Particles with a glass substrate coated with nickel/chromium/molybdenum alloy are sold under the name Crystal Star GF 550 and GF 2525 by this same company.

Irrespective of their shape, the reflective particles may also be chosen from particles with a synthetic substrate coated at least partially with at least one layer of at least one metallic compound, especially a metal oxide, chosen, for example, from titanium oxides, especially $TiO_2$, iron oxides, especially $Fe_2O_3$, tin oxide, chromium oxide, barium sulfate and the following compounds: $MgF_2$, $CrF_3$, ZnS, ZnSe, $SiO_2$, $Al_2O_3$, MgO, $Y_2O_3$, $SeO_3$, SiO, $HfO_2$, $ZrO_2$, $CeO_2$, $Nb_2O_5$, $Ta_2O_5$, $MoS_2$ and mixtures or alloys thereof.

Examples of such particles that may be mentioned include particles comprising a synthetic mica substrate coated with titanium dioxide, or particles of glass coated either with brown iron oxide or with titanium oxide, tin oxide or a mixture thereof, for instance those sold under the brand name Reflecks® by Engelhard.

Pigments of the Metashine 1080R range sold by Nippon Sheet Glass Co. Ltd., are also suitable for the invention. These pigments, described more particularly in patent application JP 2001-11340, are flakes of C-Glass comprising 65% to 72% $SiO_2$, coated with a layer of titanium oxide of rutile type ($TiO_2$). These glass flakes have a mean thickness of 1 micron and a mean size of 80 microns, i.e., a mean size/mean thickness ratio of 80. They have blue, green, yellow or silvery glints depending on the thickness of the $TiO_2$ layer.

Mention may also be made of particles of between 80 and 100 µm in size, comprising a synthetic mica substrate (fluorophlogopite) coated with titanium dioxide representing 12% of the total weight of the particle, sold under the name Prominence by Nihon Koken.

The reflective particles may also be chosen from particles formed by a stack of at least two layers with different refractive indices.

These layers may be of polymeric or metallic nature and may especially include at least one polymer layer.

Thus, the reflective particles may be particles derived from a multilayer polymer film.

Such particles are described especially in WO 99/36477, U.S. Pat. Nos. 6,299,979 and 6,387,498.

As illustrations of the materials that can constitute the various layers of the multilayer structure, it is possible to mention, this list not being limiting: polyethylene naphthalate (PEN) and its isomers, for example 2,6-, 1,4-, 1,5-, 2,7- and 2,3-PEN, polyalkylene terephthalates, polyimides, polyetherimides, atactic polystyrenes, polycarbonates, polyalkyl methacrylates and polyalkyl acrylates, syndiotactic polystyrene (sPS), syndiotactic poly-alpha-methylstyrenes, syndiotactic polydichlorostyrene, copolymers and blends of these polystyrenes, cellulose derivatives, polyalkylene polymers, fluoropolymers, chloropolymers, polysulfones, polyethersulfones, polyacrylonitriles, polyamides, silicone resins, epoxy resins, polyvinyl acetate, polyetheramides, ionomeric resins, elastomers and polyurethanes. Copolymers are also suitable, for example copolymers of PEN (for example copolymers of 2,6-, 1,4-, 1,5-, 2,7-, and/or 2,3-naphthalenedicarboxylic acid or the esters thereof with (a) terephthalic acid or its esters; (b) isophthalic acid or its esters; (c) phthalic acid or its esters; (d) alkane glycols; (e) cycloalkane glycols (for example cyclohexanedimethanol diol); (f) alkanedicarboxylic acids; and/or (g) cycloalkanedicarboxylic acids, polyalkylene terephthalate copolymers and styrene copolymers. In addition, each individual layer may include blends of two or more of the above polymers or copolymers.

The choice of materials intended to constitute the various layers of the multilayer structure is, of course, made so as to give the particles thus formed the desired reflective appearance.

Reflective particles comprising a stack of at least two layers of polymers are sold by 3M under the name Mirror Glitter. These particles comprise layers of 2,6-PEN and of polymethyl methacrylate in an 80/20 mass ratio. Such particles are described in U.S. Pat. No. 5,825,643.

The gloss of the reflective particles may also be due, as a variant or additionally, to the reflection of light on a layer of a material of the particle that has a sufficiently large refractive index relative to that of the medium from which the incident light originates.

The cosmetic composition according to the invention may, of course, comprise reflective particles of different nature without departing from the scope of the present invention.

Examples of Goniochromatic Coloring Agents:

The composition contains one or more goniochromatic coloring agents to create, when the composition is applied to its support, a colored background whose color changes with the angle of observation and with which the reflective particles contrast. A single goniochromatic coloring agent may be used for ease of implementation.

The goniochromatic coloring agent may be present, for example, in an amount that may range, on a weight basis relative to the total weight of the composition, from 0.1% to 20% or from 2% to 15% and better still from 2% to 10%, especially for a composition intended to be applied to the lips. In the case of such a composition, very satisfactory results have been obtained for a content of goniochromatic coloring agent of between 2% and 8% combined with a content of reflective particles of between 1% and 5% by weight. A nail varnish composition may contain, for example, from 0.1% to 5% of goniochromatic coloring agent; a foundation may contain from 10% to 15% thereof and a lipstick may contain from 2% to 8% thereof by weight.

The goniochromatic coloring agent may be chosen so as to present a relatively large color change with the angle of observation.

The goniochromatic coloring agent may thus be chosen such that a color difference $\Delta E$ of the cosmetic composition, measured in the CIE 1976 colorimetric space, of at least 2 may be observed for a variation of the angle of observation of between 0° and 80° under illumination at 45°.

The goniochromatic coloring agent may also be chosen such that a variation Dh of the hue angle of the cosmetic composition, in the CIE 1976 plane, of at least 30° or even at least 40° or at least 60°, or even at least 100°, may be observed for an illumination at 45° and a variation of the angle of observation of between 0° and 80°.

The goniochromatic coloring agent may be chosen, for example, from multilayer interference structures and liquid-crystal coloring agents.

In the case of a multilayer structure, it may comprise, for example, at least two layers, each layer, which may or may not be independent of the other layer(s), being made, for example, from at least one material chosen from the group consisting of the following materials: $MgF_2$, $CeF_3$, ZnS, ZnSe, Si, $SiO_2$, Ge, Te, $Fe_2O_3$, Pt, Va, $Al_2O_3$, MgO, $Y_2O_3$, $S_2O_3$, SiO, $HfO_2$, $ZrO_2$, $CeO_2$, $Nb_2O_5$, $Ta_2O_5$, $TiO_2$, Ag, Al, Au, Cu, Rb, Ti, Ta, W, Zn, $MoS_2$, cryolite, and alloys, polymers and combinations thereof.

The multilayer structure may or may not have, relative to a central layer, symmetry in the chemical nature of the stacked layers.

Examples of symmetrical multilayer interference structures that may be used in the compositions prepared in accordance with the invention are, for example, the following structures: $Al/SiO_2/Al/SiO_2/Al$, pigments having this structure being sold by Dupont de Nemours; $Cr/MgF_2/Al/MgF_2/$ Cr, pigments having this structure being sold under the name Chromaflair by Flex; $MoS_2/SiO_2/Al/SiO_2/MoS_2$; $Fe_2O_3/SiO_2/Al/SiO_2/Fe_2O_3$, and $Fe_2O_3/SiO_2/Fe_2O_3/SiO_2/Fe_2O_3$, pigments having these structures being sold under the name Sicopearl by BASF; $MoS_2/SiO_2/$mica-oxide$/SiO_2/MoS_2$; $Fe_2O_3/SiO_2/$mica-oxide$/SiO_2/Fe_2O_3$; $TiO_2/SiO_2/TiO_2$, $TiO_2/Al_2O_3/TiO_2$, $SnO/TiO_2/SiO_2/TiO_2/SnO$, $Fe_2O_3/SiO_2/Fe_2O_3$, $SnO/Mica/TiO_2/SiO_2/TiO_2/Mica/SnO$, pigments having these structures being sold under the name Xirona by Merck (Darmstadt). For example these pigments can be the pigments of silica/titanium oxide/tin oxide structure sold under the name Xirona Magic by Merck, pigments of silica/brown iron oxide structure sold under the name Xirona Indian Summer by Merck, and pigments of silica/titanium oxide/mica/tin oxide structure sold under the name Xirona Carribean Blue by Merck. Mention may also be made of the Infinite Colors pigments from the company Shiseido. Depending on the thickness and the nature of the various layers, different effects are obtained. Thus, with the $Fe_2O_3/SiO_2/Al/SiO_2/Fe_2O_3$ structure, the color changes from green-golden to red-grey for $SiO_2$ layers of 320 to 350 nm; from red to golden for $SiO_2$ layers of 380 to 400 nm; from violet to green for $SiO_2$ layers of 410 to 420 nm; from copper to red for $SiO_2$ layers of 430 to 440 nm.

Goniochromatic coloring agents with a multilayer structure comprising an alternation of polymer layers, for example of the type such as polyethylene naphthalate and polyethylene terephthalate, may also be used. Such agents are described especially in WO-A-96/19347 and WO-A-99/36478.

Examples of pigments with a polymeric multilayer structure that may be mentioned include those sold by 3M under the name Color Glitter.

The liquid-crystal coloring agents comprise, for example, silicones or cellulose ethers onto which are grafted mesomorphic groups.

Examples of liquid-crystal goniochromatic particles that may be used include, for example, those sold by Chenix and also the products sold under the name Helicone® HC by Wacker.

The composition may also comprise dispersed goniochromatic fibers. Such fibers may, for example, have a size of between 200 μm and 700 μm, for example about 300 μm.

Interference fibers with a multilayer structure may be used in particular. Fibers with a multilayer structure of polymers are described especially in EP-A-921,217, EP-A-686,858 and U.S. Pat. No. 5,472,798. The multilayer structure may comprise at least two layers, each layer, which may or may not be independent of the other layer(s), being made of at least one synthetic polymer. The polymers present in the fibers may have a refractive index ranging from 1.30 to 1.82 and better still ranging from 1.35 to 1.75. The polymers that are preferred for making the fibers are polyesters such as polyethylene terephthalate, polyethylene naphthalate, polycarbonate; acrylic polymers such as polymethyl methacrylate; polyamides.

Goniochromatic fibers with a polyethylene terephthalate/nylon-6 two-layer structure are sold by Teijin under the name Morphotex.

Gloss Base:

The composition may also comprise at least one compound capable of giving it gloss, and especially an oily phase, in particular an oily phase with a refractive index of between 1.47 and 1.51 and better still between 1.48 and 1.50. The refractive index is measured at room temperature (25° C.) using a refractometer.

Such an oily phase may prove to be useful especially in the case of a liquid gloss.

According to one implementation example of the invention, the gloss base selected is one as described in EP-A-792,637, the content of which is incorporated by reference into the present patent application.

The cosmetic composition may contain, for example, at least one carbon-based oil, hydrocarbon-based oil, fluorooil and/or silicone oil of mineral, plant or synthetic origin.

The term "hydrocarbon-based oil" means oils mainly containing carbon atoms and hydrogen atoms and in particular alkyl or alkenyl chains, for instance alkanes or alkenes, but also oils with an alkyl or alkenyl chain comprising one or more alcohol, ether, ester and/or carboxylic acid groups.

As oils that may be used, mention may thus be made, this list not being limiting, of hydrocarbon-based oils of mineral or synthetic origin such as linear or branched hydrocarbons, for instance liquid paraffin and its derivatives, liquid petroleum jelly, polydecenes, hydrogenated polyisobutene such as Parleam sold by Nippon Oil Fats, squalane of synthetic or plant origin; oils of animal origin, such as mink oil, turtle oil or perhydrosqualene; hydro-carbon-based oils of plant origin with a high triglyceride content consisting of fatty acid esters of glycerol, the fatty acids of which may have varied chain lengths, said chains possibly being linear or branched, and saturated or unsaturated, for instance sweet almond oil, beauty-leaf oil, palm oil, grapeseed oil, sesame oil, arara oil, rapeseed oil, sunflower oil, cottonseed oil, apricot oil, castor oil, alfalfa oil, marrow oil, blackcurrant oil, macadamia oil, musk rose oil, hazelnut oil, avocado oil, jojoba oil, olive oil or cereal germ oil (from corn, wheat, barley or rye); fatty acid esters and especially esters of lanolic acid, of oleic acid, of lauric acid or of stearic acid; synthetic esters such as, for example, purcellin oil (cetostearyl octanoate), isononyl isononanoate, $C_{12}$ to $C_{15}$ alkyl benzoate, 2-ethylhexyl palmitate, octanoates, decanoates or ricinoleates of alcohols or of polyalcohols, isopropyl myristate, isopropyl palmitate, butyl stearate, hexyl laurate, diisopropyl adipate, 2-ethylhexyl palmitate, 2-hexyldecyl laurate, 2-octyldecyl palmitate, 2-octyl-dodecyl myristate, 2-diethylhexyl succinate, diiso-stearyl malate, or glyceryl or diglyceryl triiso-stearate; hydroxylated esters, for instance isostearyl lactate; pentaerythritol esters; $C_8$-$C_{26}$ higher fatty acids such as oleic acid, linoleic acid, linolenic acid or isostearic acid; $C_8$-$C_{26}$ higher fatty alcohols such as oleyl alcohol, linoleyl alcohol, linolenyl alcohol, isostearyl alcohol or octyldodecanol; synthetic esters containing at least 7 carbon atoms, silicone oils such as polydimethylsiloxanes (PDMSs) that are liquid at room temperature, linear, and optionally phenylated, such as phenyltrimethicones, phenyltrimethylsiloxydi-phenylsiloxanes, diphenyldimethicones, diphenylmethyl-diphenyltrisiloxanes, liquid 2-phenylethyl trimethyl-siloxysilicates, optionally substituted with aliphatic and/or aromatic groups, for instance alkyl, alkoxy or phenyl groups that are pendent and/or at the end of a silicone chain, these groups containing from 2 to 24 carbon atoms and being optionally fluorinated, or with functional groups such as hydroxyl, thiol and/or amine groups; polysiloxanes modified with fatty acids, with fatty alcohols or with polyoxyalkylenes, for instance dimethicone copolyols or alkylmethicone copolyols; liquid fluorosilicones; or caprylic/capric acid triglycerides, for instance those sold by Stearineries Dubois or those sold under the names Miglyol 810, 812 and 818 by Dynamit Nobel; and mixtures thereof.

Good dispersion of the pigments and/or fillers in the cosmetic composition may also improve the gloss of the layer of composition applied to its support.

In the case of a nail varnish, the gloss may be obtained by introducing compounds of polyurethane and latex type, for example, into the varnish composition.

Non-Goniochromatic Coloring Agents:

The cosmetic composition may incorporate one or more non-goniochromatic coloring agents not consisting of reflective particles, chosen, for example, from dyes, especially liposoluble or water-soluble dyes, monochromatic pigments and nacres conventionally used in cosmetic compositions.

As dyes that may be used, examples that may be mentioned include Sudan red, DC Red 17, DC Green 6, P-carotene, soybean oil, Sudan brown, DC Yellow 11, DC Violet 2, DC orange 5, quinoline yellow, annatto, carotenoide derivatives, for instance lycopene, beta-carotene, bixin and capsanthin, and/or mixtures thereof, these dyes being liposoluble. Water-soluble dyes, for instance copper sulfate, iron sulfate, water-soluble sulfopolyesters such as those described in FR-96,154, 152, rhodamines, natural dyes (carotene, beetroot juice), methylene blue and caramel, may also be used.

The dyes may represent, for example, from 0.01% to 20% and better still from 0.1% to 10% of the total weight of the composition.

As pigments that may be used, mention may be made of pigments consisting of white or colored particles, intended, for example, to color and/or opacify the composition. Among the pigments that may be used, mention may be made of carbon black, barium, strontium, calcium and aluminum lakes, titanium oxide, zirconium oxide, cerium oxide, zinc oxide, iron oxide or chromium oxide and ferric blue.

Nacres may be present in the composition in a proportion, for example, of from 0 to 20% of the total weight of the composition, or even in a content of about from 1% to 15%. Examples of nacres that may be mentioned include natural mica coated with titanium oxide, with iron oxide, with natural pigment or with bismuth oxychloride. Among the commercially available nacres that may be mentioned are the nacres Timica and Flamenco sold by Engelhard and the Timiron nacres sold by Merck.

The non-goniochromatic coloring agents may represent, for example, from 0.001% to 60%, preferably from 0.01% to 50% and better still from 0.1% to 40% of the total weight of the composition. For pulverulent compositions, the amount of coloring agents may be up to 85% and even up to 98%.

Physiologically Acceptable Medium:

The physiologically acceptable medium will be adapted to the nature of the support to which the composition is to be applied, and also to the form in which the composition is intended to be packaged, especially solid or fluid at room temperature and atmospheric pressure.

The composition according to the invention may comprise an aqueous cosmetic medium and/or a fatty phase.

The composition may comprise water or a mixture of water and hydrophilic organic solvents, for instance alcohols and especially linear or branched lower monoalcohols containing from 2 to 5 carbon atoms, for instance ethanol, isopropanol or n-propanol, polyols, for instance glycerol, diglycerol, propylene glycol, sorbitol, pentylene glycol and polyethylene glycols. The hydrophilic phase may also contain hydrophilic $C_2$ ethers and $C_2$-$C_4$ aldehydes. The water or the mixture of water and of hydrophilic organic solvents may be present in the composition according to the invention, or one of the base and/or surface compositions, in a content ranging from 0% to 90% (especially 0.1% to 90%) by weight and preferably from 0% to 60% by weight (especially 0.1% to 60% by weight), relative to the total weight of the composition.

The composition may also comprise a fatty phase consisting especially of fatty substances that are liquid at room temperature (in general 25° C.) and/or fatty substances that are solid at room temperature, such as waxes, pasty fatty substances and gums, and mixtures thereof. This fatty phase may also contain lipophilic organic solvents.

As fatty substances that are liquid at room temperature, often known as oils, which may be used in the invention, mention may be made of: hydrocarbon-based plant oils such as liquid triglycerides of fatty acids containing from 4 to 10 carbon atoms, for instance heptanoic or octanoic acid triglyceride, or alternatively sunflower oil, corn oil, soybean oil, grape seed oil, sesame seed oil, apricot oil, macadamia oil, castor oil, avocado oil, caprylic/capric acid triglycerides, jojoba oil and karite butter; linear or branched hydrocarbons of mineral or synthetic origin such as liquid paraffins and derivatives thereof, petroleum jelly, polydecenes and hydrogenated polyisobutene such as parleam; synthetic esters and synthetic ethers, especially of fatty acids, such as, for example, purcellin oil, isopropyl myristate, 2-ethylhexyl palmitate, 2-octyl-dodecyl stearate, 2-octyldodecyl erucate and isostearyl isostearate; hydroxylated esters, for instance isostearyl lactate, octyl hydroxystearate, octyldodecyl hydroxystearate, diisostearyl malate, triisocetyl citrate, and fatty alkyl heptanoates, octanoates and decanoates; polyol esters, for instance propylene glycol dioctanoate, neopentyl glycol diheptanoate or diethylene glycol diisononanoate; and pentaerythritol esters; fatty alcohols containing from 12 to 26 carbon atoms, for instance octyldodecanol, 2-butyloctanol, 2-hexyldecanol, 2-undecylpentadecanol and oleyl alcohol; partially hydrocarbon-based or silicone-based fluoro oils; silicone oils, for instance linear or cyclic, volatile or non-volatile polydimethylsiloxanes (PDMSs) that are liquid or pasty at room temperature, for instance cyclomethicones, dimethicones, optionally comprising a phenyl group, for instance phenyl trimethicones, phenyltrimethylsiloxydiphenyl siloxanes, diphenylmethyldimethyl-trisiloxanes, diphenyl dimethicones, phenyl dimethicones and polymethylphenylsiloxanes; mixtures thereof.

These oils may be present in a content ranging from 0.01% to 90% and better still from 0.1% to 85% by weight, relative to the total weight of the composition.

The composition of the invention may also advantageously comprise a fatty substance that is solid or pasty at room temperature, for instance gums or waxes. The waxes may be hydrocarbon-based waxes, fluoro waxes and/or silicone waxes and may be of plant, mineral, animal and/or synthetic origin. In particular, the waxes may have a melting point of greater than 25° C. and preferably greater than 45° C.

As waxes that may be used in the composition of the invention, mention may be made of beeswax, carnauba wax or candelilla wax, paraffin, microcrystalline waxes, ceresin or ozokerite; synthetic waxes, for instance polyethylene waxes or Fischer-Tropsch waxes, or silicone waxes, for instance alkyl dimethicones or alkoxy dimethicones containing from 16 to 45 carbon atoms.

The gums are generally polydimethylsiloxanes (PDMSs) of high molecular weight or cellulose gums or polysaccharides and the pasty substances are generally hydrocarbon-based compounds, for instance lanolins and derivatives thereof, or PDMSs.

The nature and amount of the solid substances depend on the desired mechanical properties and textures. As a guide, the composition may contain from 0% to 50% by weight and better still from 1% to 30% by weight of waxes, relative to the total weight of the composition.

The composition according to the invention may also comprise one or more physiologically acceptable organic solvents. These solvents may be present in a content ranging from 0% to 90%, better still from 0% to 60% and even better still from 0.1% to 30% by weight, relative to the total weight of the composition.

The presence of organic solvents is more particularly suitable for making up the nails. The composition then generally constitutes a nail varnish. The organic solvent may be present in the cosmetic composition in a content ranging, for example, from 30% to 99% by weight and preferably from 60% to 90% by weight relative to the total weight of the composition.

When the physiologically acceptable medium of the composition contains a liquid phase, this phase may especially be a liquid organic phase in which water is dispersed or emulsified.

The composition may have a continuous fatty phase, which may contain less than 5% water, especially less than 1% water, relative to its total weight, and in particular may be in anhydrous form.

Fillers:

The cosmetic composition may also comprise fillers.

The term "fillers" denotes particles of any form that are insoluble in the medium of the composition, irrespective of the temperature at which the composition is manufactured. These fillers especially serve to modify the rheology or texture of the composition.

Examples of fillers that may be mentioned, inter alia, are talc, mica, silica, kaolin and polyamide (Nylon®) powders (Orgasol® from Atochem).

Cosmetic Active Agents:

The cosmetic composition may also contain one or more cosmetic, dermatological, hygiene or pharmaceutical active agents.

As cosmetic, dermatological, hygiene or pharmaceutical active agents that may be used in the compositions of the invention, mention may be made of moisturizers (polyols, for instance glycerol), vitamins (C, A, E, F, B, or PP) essential fatty acids, essential oils, ceramides, sphingolipids, liposoluble sunscreens or sunscreens in the form of nanoparticles, and specific active agents for treating the skin (protective agents, antibacterial agents, anti-wrinkle agents, etc.). These active agents may be used, for example, in concentrations of from 0% to 20% and especially from 0.001% to 15% relative to the total weight of the composition.

The cosmetic composition may also contain ingredients commonly used in cosmetics, for instance thickeners, surfactants, trace elements, moisturizers, softeners, sequestering agents, fragrances, acidifying or basifying agents, preservatives, antioxidants and UV-screening agents, or mixtures thereof.

Depending on the type of application envisaged, the cosmetic composition may furthermore comprise constituents conventionally used in the fields under consideration, which are present in an amount that is suitable for the desired presentation form.

The cosmetic composition may be in any presentation form normally used for topical application, and especially in anhydrous form or in the form of an oily or aqueous solution, an oily or aqueous gel, an oil-in-water or water-in-oil emulsion, a multiple emulsion or a dispersion of oil in water by means of vesicles located at the oil/water interface.

The composition of the invention may be in powder, liquid, solid or semi-solid form, especially in the form of a product cast as a stick or a dish, or in the form of a tube, a paste or a more or less fluid cream.

The cosmetic composition may constitute, inter alia, a lipstick, a liquid gloss, a lipstick paste, a makeup rouge, a lip pencil, a solid or fluid foundation, a concealer product, a product for the contour of the eyes, an eyeliner, a mascara, a nail varnish, an eyeshadow, a makeup product for the body or the hair or an antisun product or skin-coloring product.

The composition of the invention may be obtained according to the preparation processes conventionally used in cosmetics.

In order to further illustrate the present invention and the advantages thereof, the following specific examples are given, it being understood that same are intended only as illustrative and in nowise limitative.

EXAMPLES

The percentages below are all expressed on a weight basis relative to the total weight of the composition.

The invention applies most particularly to compositions intended to be applied to the lips.

To check the optical properties of a composition prepared in accordance with the invention, a liquid gloss having the composition below was prepared.

| Liquid gloss: | |
|---|---|
| Poly(bis(diglyceryl) 2-acryladipate) | 17.5 |
| Diisostearyl malate | 9.5 |
| Tridecyl trimellitate | 10 |
| $C_{18}$-$C_{36}$ acid triglyceride | 19 |
| Dimethyl silylate silica | 8 |
| Silver-coated glass particles (Metashine ®)* | 2 |
| Goniochromatic pigment (Sicopearl ®)** | 5 |
| Nacre | 3 |
| Polybutene | 12 |
| Pentaerythrityl tetraisostearate | 13 |
| Fragrance, preservatives | qs |

*sold by Toyal
**sold by BASF

Figure 2:
FIG. 2 is a photograph of made-up lips with a liquid gloss prepared in accordance with the invention. The lips look "fuller". The presence of numerous highlight points and the high mean gloss of the composition are to be noted.

After application, it is found that the composition makes the lips "fuller". FIG. 2 is a photograph of made-up lips. The presence of numerous highlight points and the high mean gloss of the composition may be noted in the photograph.

A semi-solid lipstick was also prepared.

| Lipstick in tube form: | |
|---|---|
| Octyldodecyl neopentanoate | 17.0 |
| Capric/caprylic acid triglyceride | 10.2 |
| Lanolin oil | 15.0 |
| Acetylated lanolin | 10.2 |
| Polybutene | 15.0 |
| Silver-coated glass particles (Metashine ® REFSX) | 4.0 |
| Goniochromatic pigment (Sicopearl ® | 3.0 |
| Microcrystalline wax | 2.5 |
| Polyethylene wax | 7.4 |
| Phenyltrimethicone | 7.0 |
| Hydrogenated polyisobutene | 6.5 |
| Fragrance, preservative, antioxidant | qs |

Procedure: The betone is dispersed in some of the oily phase, the rest of the fatty phase is then added and the mixture is heated to 95° C. After homogenization and grinding of the pigments, the mixture is cast in suitable moulds.

Tubes of lipstick are obtained, which give an impression of volume after application to the lips. The composition also has good application properties.

The invention is not limited to compositions intended to be applied to the lips, and other examples of compositions will be given by way of illustration.

Nail Varnish:

A nail varnish having the composition below was prepared:

| | |
|---|---|
| Nitrocellulose | 10 |
| Plasticizers and resin | 15 |
| Rheological agent | 1.5 |
| Silver-coated glass particles (Metashine ® REFSX) | 5 |
| Goniochromatic pigment (Sicopearl ®) | 2 |
| Ethyl acetate, butyl acetate | qs 100 |

The composition is applied to the nails. A pink makeup result with "metallic" gloss points is obtained.

| Eyeshadow: | |
|---|---|
| Silver-coated glass particles (Metashine ® REFSX) | 5 |
| Goniochromatic pigment (Sicopearl ®) | 10 |
| Silica | 1.5 |
| Triethanolamine | 1 |
| Carbomer | 0.5 |
| Polyvinylpyrrolidone | 1 |
| Butylene glycol | 2 |
| Glycerol | 5 |
| Preservatives | qs |
| Water | qs 100 |

Once applied to the eyelids, the composition produces a colored makeup result with "metallic" gloss points.

Needless to say, the invention is not limited to the implementation examples that have just been described.

It is especially possible to prepare, in accordance with the invention, a composition comprising goniochromatic coloring agents of different nature and also reflective particles of different nature.

Throughout the description, including the claims, the expression "comprising a" should be understood as being synonymous with "comprising at least one", unless otherwise specified.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A goniochromatic/light reflecting cosmetic makeup composition, comprising: (a) at least one goniochromatic coloring agent, wherein said at least one goniochromatic coloring agent is such that a variation Dh of the hue angle thereof of at least 30° is observed on a layer of such cosmetic makeup composition, for an illumination at 45° and a variation of the angle of observation of between 0° and 80°, and wherein said at least one goniochromatic coloring agent is present in an amount ranging from 0.1% to 20% of the total weight of the composition; and (b) an amount of light reflective particles different from said at least one goniochromatic coloring agent, wherein the light reflective particles are particles of a synthetic substrate made from glasses, the light reflective particles are at least partially coated with at least one layer of at least one metallic compound, said light reflective particles having a spectral reflectance in the visible spectrum of at least 70% and not being greater than 250 μm in size, and being present in the composition in an amount ranging from 0.1% to 20% by weight relative to the total weight of the composition, formulated into (c) a topically applicable, physiologically acceptable medium therefor, said composition having a mean gloss greater than or equal to 30 and creating an optical volumizing effect once applied to a support or a substrate.

2. The cosmetic makeup composition as defined by claim 1, said at least one metallic compound comprising a metal oxide.

3. The cosmetic makeup composition as defined by claim 2, said at least one metallic compound being selected from the group consisting of titanium oxides, iron oxides, tin oxide, chromium oxide, barium sulfate, $MgF_2$, $CeF_3$, ZnS, ZnSe, $SiO_2$, $Al_2O_3$, MgO, $Y_2O_3$, $SeO_3$, SiO, $HfO_2$, $ZrO_2$, $CeO_2$, $Nb_2O_5$, $Ta_2O_5$ and $MoS_2$, and mixtures thereof.

4. The cosmetic makeup composition as defined by claim 3, said at least one metallic compound being selected from the group consisting of titanium oxide, iron oxide, tin oxide and mixtures thereof.

5. The cosmetic makeup composition as defined by claim 4, said at least one metallic compound being $TiO_2$.

6. The cosmetic makeup composition as defined by claim 1, having a mean gloss greater than or equal to 50.

7. The cosmetic makeup composition as defined by claim 6, having a mean gloss greater than or equal to 70.

8. The cosmetic makeup composition as defined by claim 1, wherein said at least one goniochromatic coloring agent is such that a variation Dh of the hue angle thereof of at least 60° is observed on a layer of such cosmetic makeup composition for an illumination at 45° and a variation of the angle of observation of between 0° and 80°.

9. The cosmetic makeup composition as defined by claim 1, said reflective particles being less than 150 μm in size.

10. The cosmetic makeup composition as defined by claim 9, said reflective particles being less than 100 μm in size.

11. The cosmetic makeup composition as defined by claim 10, said reflective particles being at least 10 μm in size.

12. The cosmetic makeup composition as defined by claim 1, said reflective particles ranging from 20 μm to 50 μm in size.

13. The cosmetic makeup composition as defined by claim 1, said reflective particles being present in the composition in an amount ranging from 1% to 15% by weight relative to the total weight of the composition.

14. The cosmetic makeup composition as defined by claim 13, said reflective particles being present in the composition in an amount ranging from 1% to 10% by weight relative to the total weight of the composition.

15. The cosmetic makeup composition as defined by claim 1, said reflective particles being in the form of platelets or spheres.

16. The cosmetic makeup composition as defined by claim 1, said at least one goniochromatic coloring agent comprising a liquid-crystal coloring agent or a multilayer interference structure.

17. The cosmetic makeup composition as defined by claim 1, said at least one goniochromatic coloring agent comprising a multilayer interference structure selected from the group of structures consisting of $Al/SiO_2/Al/SiO_2/Al$; $Cr/MgF_2/Al/MgF_2/Cr$; $MoS_2/SiO_2/Al/SiO_2/MoS_2$; $Fe_2O_3/SiO_2/Al/SiO_2/Fe_2O_3$; $Fe_2O_3/SiO_2/Fe_2O_3/SiO_2/Fe_2O_3$; $MOS_2/SiO_2/mica-oxide/SiO_2/MOS_2$; $Fe_2O_3/SiO_2/mica-oxide/SiO_2/Fe_2O_3$, $TiO_2/SiO_2/TiO_2$; $TiO_2/Al_2O_3/TiO_2$, $SnO/TiO_2/SiO_2/TiO_2/SnO$, $Fe_2O_3/SiO_2/Fe_2O_3$ and $SnO/Mica/TiO_2/SiO_2/TiO_2/Mica/SnO$.

18. The cosmetic makeup composition as defined by claim 17, said at least one goniochromatic coloring agent comprising a multilayer interference structure selected from the group of structures consisting of $MoS_2/SiO_2/Al/SiO_2/MoS_2$; $Fe_2O_3/SiO_2/Al/SiO_2/Fe_2O_3$ and $Fe_2O_3/SiO_2/Fe_2O_3/SiO_2/Fe_2O_3$; $SnO/TiO_2/SiO_2/TiO_2/SnO$, $Fe_2O_3/SiO_2/Fe_2O_3$ and $SnO/Mica/TiO_2/SiO_2/TiO_2/Mica/SnO$.

19. The cosmetic makeup composition as defined by claim 1, said at least one goniochromatic coloring agent being present in an amount ranging from 2% to 15% of the total weight of the composition.

20. The cosmetic makeup composition as defined by claim 19, said at least one goniochromatic coloring agent being present in an amount ranging from 2% to 10% of the total weight of the composition.

21. The cosmetic makeup composition as defined by claim 1, comprising a gloss base having a mean gloss of greater than 20.

22. The cosmetic makeup composition as defined by claim 21, comprising a gloss base having a mean gloss of greater than 50.

23. The cosmetic makeup composition as defined by claim 22, comprising a gloss base having a mean gloss of greater than 70.

24. The cosmetic makeup composition as defined by claim 1, comprising an oily phase having a refractive index of between 1.47 and 1.51.

25. The cosmetic makeup composition as defined by claim 1, further comprising at least one non-goniochromatic coloring agent.

26. The cosmetic makeup composition as defined by claim 25, said at least one non-goniochromatic coloring agent being selected from the group consisting of dyes, monochromatic pigments and nacres.

27. The cosmetic makeup composition as defined by claim 1, comprising goniochromatic fibers.

28. The cosmetic makeup composition as defined by claim 1, formulated in anhydrous form, in the form of an oily or aqueous solution, an oily or aqueous gel, an oil-in-water or water-in-oil emulsion, a multiple emulsion, a dispersion of oil in water by means of vesicles located at the oil/water interface.

29. A liquid gloss comprising the cosmetic makeup composition as defined by claim 1.

30. A lip makeup comprising the cosmetic makeup composition as defined by claim 1.

31. A nail varnish comprising the cosmetic makeup composition as defined by claim 1.

32. A foundation comprising the cosmetic makeup composition as defined by claim 1.

33. A mascara comprising the cosmetic makeup composition as defined by claim 1.

34. A method of using a goniochromatic/light reflecting cosmetic makeup composition, the composition comprising: (a) at least one goniochromatic coloring agent, wherein said at least one goniochromatic coloring agent is such that a variation Dh of the hue angle thereof of at least 30° is observed on a layer of such cosmetic makeup composition, for an illumination at 45° and a variation of the angle of observation of between 0° and 80°, and wherein said at least one goniochromatic coloring agent is present in an amount ranging from 0.1% to 20% of the total weight of the composition; and (b) an amount of light reflective particles different from said at least one goniochromatic coloring agent, wherein the light reflective particles are particles of a synthetic substrate made from glasses and the light reflective particles are at least partially coated with at least one layer of at least one metallic compound, said light reflective particles having a spectral reflectance in the visible spectrum of at least 70% and not being greater than 250 µm in size, and being present in the composition in an amount ranging from 0.1% to 20% by weight relative to the total weight of the composition, formulated into (c) a topically applicable, physiologically acceptable medium therefor, said composition having a mean gloss greater than or equal to 30, the method comprising: applying said goniochromatic/light reflecting cosmetic makeup composition to a support or a substrate creating an optical volumizing effect once applied to the support or substrate.

35. The method of using the goniochromatic/light reflecting cosmetic makeup composition of claim 34, wherein said at least one metallic compound comprises a metal oxide.

36. The method of using the goniochromatic/light reflecting cosmetic makeup composition of claim 34, wherein said at least one metallic compound is selected from the group consisting of titanium oxides, iron oxides, tin oxide, chromium oxide, barium sulfate, $MgF_2$, $CeF_3$, ZnS, ZnSe, $SiO_2$, $Al_2O_3$, MgO, $Y_2O_3$, $SeO_3$, SiO, $HfO_2$, $ZrO_2$, $CeO_2$, $Nb_2O_5$, $Ta_2O_5$ and $MoS_2$, and mixtures thereof.

37. The method of using the goniochromatic/light reflecting cosmetic makeup composition of claim 36, wherein said at least one metallic compound is selected from the group consisting of titanium oxide, iron oxide, tin oxide and mixtures thereof.

38. The method of using the goniochromatic/light reflecting cosmetic makeup composition of claim 37, wherein said at least one metallic compound is $TiO_2$.

39. The method of using the goniochromatic/light reflecting cosmetic makeup composition of claim 34, wherein said cosmetic makeup composition has a mean gloss greater than or equal to 50.

40. The method of using the goniochromatic/light reflecting cosmetic makeup composition of claim 39, wherein said cosmetic makeup composition has a mean gloss greater than or equal to 70.

41. The method of using the goniochromatic/light reflecting cosmetic makeup composition of claim 34, wherein said goniochromatic coloring agent is such that a variation Dh of the hue angle thereof of at least 60° is observed on a layer of such cosmetic makeup composition for an illumination at 45° and a variation of the angle of observation of between 0° and 80°.

42. The method of using the goniochromatic/light reflecting cosmetic makeup composition of claim 34, wherein said reflective particles are from 20 µm to 50 µm in size.

43. The method of using the goniochromatic/light reflecting cosmetic makeup composition of claim 34, wherein said reflective particles are present in the composition in an amount ranging from 1% to 15% by weight relative to the total weight of the composition.

44. The method of using the goniochromatic/light reflecting cosmetic makeup composition of claim 43, wherein said reflective particles are present in the composition in an amount ranging from 1% to 10% by weight relative to the total weight of the composition.

45. The method of using the goniochromatic/light reflecting cosmetic makeup composition of claim 34, wherein said reflective particles are in the form of platelets or spheres.

46. The method of using the goniochromatic/light reflecting cosmetic makeup composition of claim 34, wherein said at least one goniochromatic coloring agent comprises a liquid-crystal coloring agent or a multilayer interference structure.

47. The method of using the goniochromatic/light reflecting cosmetic makeup composition of claim 34, wherein said at least one goniochromatic coloring agent comprises a multilayer interference structure selected from the group of structures consisting of Al/SiO$_2$/Al/SiO$_2$/Al; Cr/MgF$_2$/Al/MgF$_2$/Cr; MoS$_2$/SiO$_2$/Al/SiO$_2$/MoS$_2$; Fe$_2$O$_3$/SiO$_2$/Al/SiO$_2$/Fe$_2$O$_3$; Fe$_2$O$_3$/SiO$_2$/Fe$_2$O$_3$/SiO$_2$/Fe$_2$O$_3$; MOS$_2$/SiO$_2$/mica-oxide/SiO$_2$/MOS$_2$; Fe$_2$O$_3$/SiO$_2$/mica-oxide/SiO$_2$/Fe$_2$O$_3$, TiO$_2$/SiO$_2$/TiO$_2$; TiO$_2$/Al$_2$O$_3$/TiO$_2$, SnO/TiO$_2$/SiO$_2$/TiO$_2$/SnO, Fe$_2$O$_3$/SiO$_2$/Fe$_2$O$_3$ and SnO/Mica/TiO$_2$/SiO$_2$/TiO$_2$/Mica/SnO.

48. The method of using the goniochromatic/light reflecting cosmetic makeup composition of claim 47, wherein said at least one goniochromatic coloring agent comprises a multilayer interference structure selected from the group of structures consisting of MoS$_2$/SiO$_2$/Al/SiO$_2$/MoS$_2$; Fe$_2$O$_3$/SiO$_2$/Al/SiO$_2$/Fe$_2$O$_3$ and Fe$_2$O$_3$/SiO$_2$/Fe$_2$O$_3$/SiO$_2$/Fe$_2$O$_3$; SnO/TiO$_2$/SiO$_2$/TiO$_2$/SnO, Fe$_2$O$_3$/SiO$_2$/Fe$_2$O$_3$ and SnO/Mica/TiO$_2$/SiO$_2$/TiO$_2$/Mica/SnO.

49. The method of using the goniochromatic/light reflecting cosmetic makeup composition of claim 34, wherein said cosmetic makeup composition comprises a gloss base having a mean gloss of greater than 20.

50. The method of using the goniochromatic/light reflecting cosmetic makeup composition of claim 49, wherein said gloss base has a mean gloss of greater than 50.

51. The method of using the goniochromatic/light reflecting cosmetic makeup composition of claim 50, wherein said gloss base has a mean gloss of greater than 70.

52. The method of using the goniochromatic/light reflecting cosmetic makeup composition of claim 34, wherein said cosmetic makeup composition comprises an oily phase having a rat-active index of between 1.47 and 1.51.

53. The method of using the goniochromatic/light reflecting cosmetic makeup composition of claim 34, wherein said cosmetic makeup composition further comprises at least one non-goniochromatic coloring agent.

54. The method of using the goniochromatic/light reflecting cosmetic makeup composition of claim 53, wherein said at least one non-goniochromatic coloring agent being selected from the group consisting of dyes, monochromatic pigments and nacres.

55. The method of using the goniochromatic/light reflecting cosmetic makeup composition of claim 53, wherein said at least one non-goniochromatic coloring agent comprises goniochromatic fibers.

56. The method of using the goniochromatic/light reflecting cosmetic makeup composition of claim 34, wherein said cosmetic makeup composition is formulated in anhydrous form, in the form of an oily or aqueous solution, an oily or aqueous gel, an oil-in-water or water-in-oil emulsion, a multiple emulsion, a dispersion of oil in water by means of vesicles located at the oil/water interface.

57. The method of using the goniochromatic/light reflecting cosmetic makeup composition of claim 34, wherein a liquid gloss comprising the cosmetic makeup composition is applied to a support or a substrate, to create a volumizing effect.

58. The method of using the goniochromatic/light reflecting cosmetic makeup composition of claim 34, wherein a lip makeup comprising the cosmetic makeup composition is applied to a support or a substrate, to create a volumizing effect.

59. The method of using the goniochromatic/light reflecting cosmetic makeup composition of claim 34, wherein a nail varnish comprising the cosmetic makeup composition is applied to a support or a substrate, to create a volumizing effect.

60. The method of using the goniochromatic/light reflecting cosmetic makeup composition of claim 34, wherein a foundation comprising the cosmetic makeup composition is applied to a support or a substrate, to create a volumizing effect.

61. The method of using the goniochromatic/light reflecting cosmetic makeup composition of claim 34, wherein a mascara comprising the cosmetic makeup composition is applied to a support or a substrate, to create a volumizing effect.

* * * * *